US00PP10543P

United States Patent [19]

Meilland

[11] Patent Number: Plant 10,543

[45] Date of Patent: Aug. 11, 1998

[54] MINIATURE ROSE PLANT NAMED 'MEIDREPIL'

[75] Inventor: Alain A. Meilland, Antibes, France

[73] Assignee: CP (Delaware), Inc., Wilmington, Del.

[21] Appl. No.: 903,763

[22] Filed: Jul. 31, 1997

[51] Int. Cl.[6] ..... A01H 5/00

[52] U.S. Cl. ..... Plt./8.2

[58] Field of Search ..... Plt./8.2

*Primary Examiner*—Howard J. Locker

*Attorney, Agent, or Firm*—Burns, Doane, Swecker & Mathis, L.L.P.

[57] ABSTRACT

A new and distinct variety of rose plant of the miniature class is provided which abundantly forms attractive small double yellow blossoms. A hanging growth habit is exhibited that renders the plant well suited for growing outdoors in a hanging basket. The plant propagates well from cuttings. The blossoms possess a slight fragrance, and the dark green foliage is semi-glossy.

1 Drawing Sheet

SUMMARY OF THE INVENTION

The new variety of miniature rose plant was created by artificial pollination wherein two parents were crossed which previously had been studied in the hope that they would contribute the desired characteristics. The female parent (i.e., the seed parent) of the new variety was the product of the pollination of the 'Meiplarzon' variety (non-patented in the United States) and the 'Meitrisical' variety (non-patented in the United States). The male parent (i.e., the pollen parent) of the new variety was the 'Katharina Zeimet' variety (non-patented in the United States). The parentage of the new variety can be summarized as follows:

('Meiplarzon'×'Meitrisical')×'Katharina Zeimet'.

The seeds resulting from the above pollination were sown and small plants were obtained which were physically and biologically different from each other. Selective study resulted in the identification of a single plant of the new variety.

It was found that the new variety of miniature rose plant of the present invention possesses the following combination of characteristics:

(a) forms in abundance attractive small yellow double blossoms,
(b) exhibits a hanging growth habit,
(c) forms semi-glossy dark green foliage,
(d) propagates well on its own roots, and
(e) is particularly suited for growing as ornamentation in a hanging basket.

The new variety well meets the needs of the horticultural industry. It is particularly well-suited for use as attractive ornamentation in the landscape or for growing as a decorative pot plant.

The new variety has been found to undergo asexual propagation in France by a number of routes, including budding, grafting, and cuttage. Asexual propagation by the above-mentioned methods as performed in France has shown that the characteristics of the new variety are strictly transmissible from one generation to another.

The new variety has been named the 'Meidrepil' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while growing on their own roots indoors at LeCannet des Maures, Var, France.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower during the course of opening;

FIG. 6 — illustrates a specimen of an open flower — plan view — obverse;

FIG. 7 — illustrates a specimen of an open flower — plant view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of leaves with three leaflets with the upper surface being shown at the top-left and the under surface being shown at the bottom-right;

FIG. 15 — illustrates specimens of leaves with five leaflets with the upper surface being shown at the bottom and the under surface being shown at the top; and FIG. 16 — illustrates specimens of leaves with seven leaflets with the upper surface being shown at the bottom-left and the under surface being shown at the top-right.

DETAILED DESCRIPTION

Figures 1, 2, 3, 4, 5, 6, 7, 8, 9, 10, 11, 12, 13, 14, 15, 16:
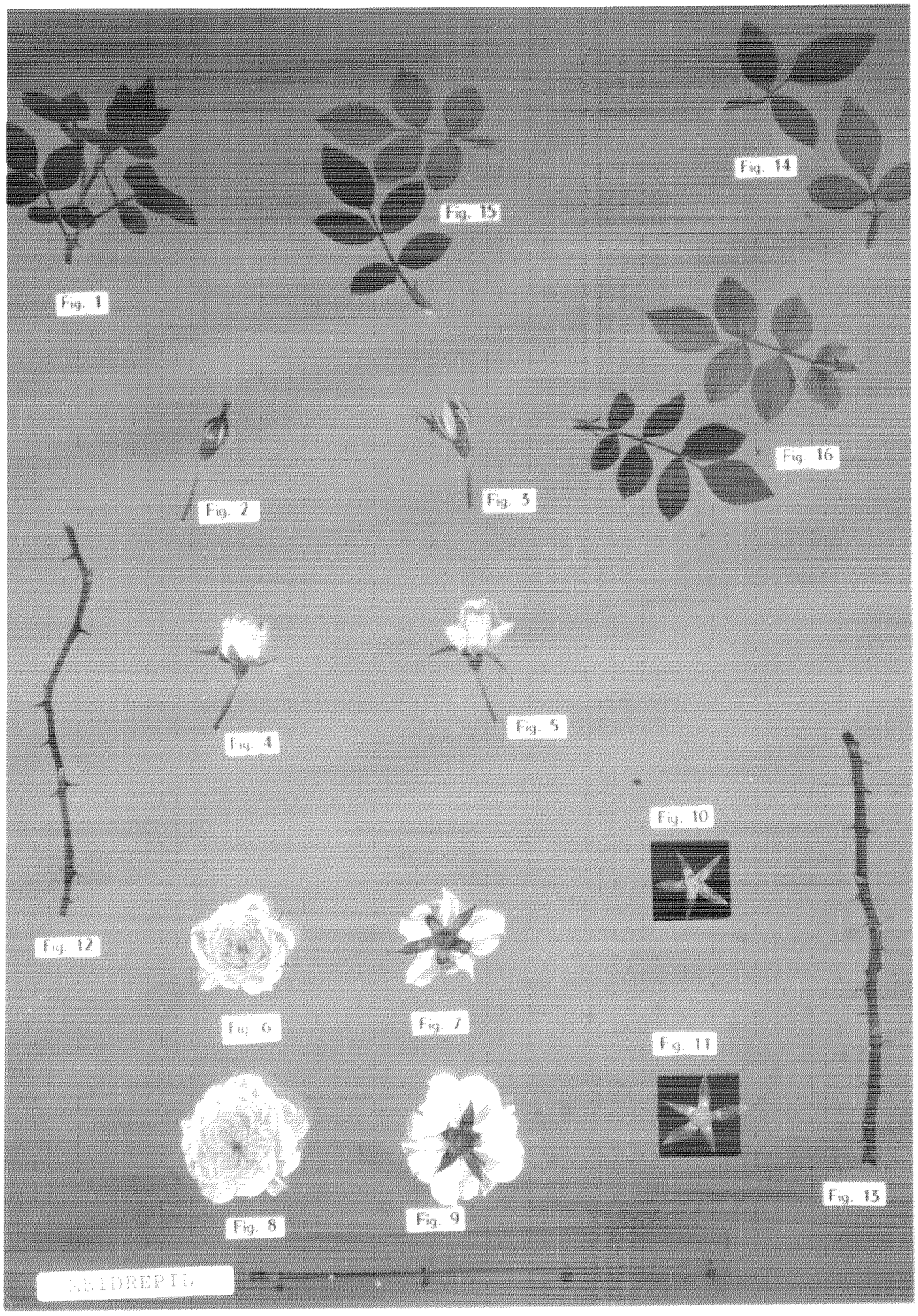

The chart used in the identification of the colors is that of The Royal Horticultural Society (R.H.S. Colour Chart). The terminology which precedes reference to the chart has been added to indicate the corresponding colors in more common terms. The description is based on two year-old specimens of the new variety which were observed during November while growing on their own roots indoors at LeCannet des Maures, Var, France.

Class: Miniature.

Plant:

*Height.*—Approximately 20 to 30 cm. on average at the end of the growing season.

*Habit.*—Hanging.

Branches:

*Color.*—Young stems: light green, Green Group 143C. Adult wood: Medium green, Green Group 143B.

*Thorns.*—Size: small. Quantity: moderately numerous. Color: pinkish.

Leaves:

*Petioles.*—Upper surface: striped, reddish on young foliage and medium green on mature foliage with more or less glandular edges. Under surface: light green and bear some small thorns.

*Stipules.*—Adnate, pectinate, narrow and linear.

*Leaflets.*—Number: 3, 5, and 7 (most often). Shape: elliptic. Texture: consistent. General appearance: very dense and semi-glossy. Color (young foliage): upper surface: light green, Green Group 137D, and more or less edged with reddish coloration. under surface: light green, Green Group 138C, and more or less tinted with reddish-brown coloration. Color (adult foliage): upper surface: dark green, Green Group 138A. under surface: medium green, Green Group 138B.

Inflorescence:

*Number of flowers.*—Commonly approximately 6 to 15 per stem.

*Peduncle*—Medium green in coloration, more or less glandular, and the length is approximately 2.5 to 3.5 cm on average.

*Sepals.*—Upper surface: tomentose, and greenish in coloration. Under surface: medium green in coloration and commonly with weak extensions.

*Buds.*—Shape: ovoid. Length: Approximately 1.5 on average. Size: small. Color upon opening: upper surface: Barium Yellow, Yellow Group 10A. under surface: Barium Yellow, Yellow Group 10B.

*Flower.*—Form: flattened. Diameter: approximately 4 to 4.5 cm on average. Color (when opening begins): upper surface: Aureolin Yellow, Yellow Group 12A. under surface: Straw Yellow, Yellow Group 13C. Color (when blooming): upper surface: Aureolin Yellow, Yellow Group 12A, becoming lighter on the external petals. under surface: Straw Yellow, Yellow Group 13C, becoming lighter on the external petals. Color (at end of opening): upper surface: Aureolin Yellow, Yellow Group 12A, becoming Empire Yellow, Yellow Group 11D. under surface: Straw Yellow, Yellow Group 13C, becoming Empire Yellow, Yellow Group 11D. Fragrance: slight. Petal number: approximately 98 to 103 on average. Petal shape: oval and very narrow near the receptacle. Petal drop: good. Anthers: normal and ochre in coloration. Stamen number: approximately 20 to 25 on average. Filaments: normal. Pistil number: approximately 19 on average. Stigmas: normal and bright yellow in coloration. Styles: greenish in coloration. Receptacle: light green, and in longitudinal section in the shape of a pitcher. Lasting quality: long on the plant.

Development:

*Vegetation.*—Very strong.

*Blooming.*—Abundant.

*Aptitude to bear fruit.*—Good.

*Resistance to diseases.*—Very good.

I claim:

1. A new and distinct variety of miniature rose plant characterized by the following combination of characteristics:

(a) forms in abundance attractive small double yellow blossoms,
(b) exhibits a hanging growth habit,
(c) forms semi-glossy dark green foliage,
(d) propagates well on its own roots, and
(e) is particularly suited for growing as ornamentation in a hanging basket;

substantially as herein shown and described.

* * * * *